United States Patent [19]

Jacobson

[11] Patent Number: 5,726,337
[45] Date of Patent: Mar. 10, 1998

[54] FLUORINATED ALKYLTHIOCYANATE PROCESS

[75] Inventor: Stephen Ernest Jacobson, Princeton Junction, N.J.

[73] Assignee: E. I. du Pont de Nemours and Company, Wilmington, Del.

[21] Appl. No.: 766,717

[22] Filed: Dec. 13, 1996

[51] Int. Cl.$^6$ .................. C07C 331/04; C07C 331/02
[52] U.S. Cl. ........................... 558/15; 558/12; 558/14
[58] Field of Search ........................... 558/12, 14, 15, 558/16

[56] References Cited

U.S. PATENT DOCUMENTS 5,565,597 10/1996 Berthe et al. ........................... 558/12

OTHER PUBLICATIONS

F. Szonyi and A. Cambdon, Functionalization of the F–Alkyl–2–Ethane Iodides by Phase Transfer Catalysis: Importance of this Technique for the F–Alkylated Series, *Journal of Fluorine Chemistry (France)*, 42, 59–68, 1989 (Original and Translation enclosed).

*Primary Examiner*—Michael G. Ambrose

[57] ABSTRACT

A process for the preparation of a thiocyanate of Formula II $$R_f-A_m-(CH_2)_n-SCN \qquad \text{II}$$

wherein $R_f$ is a $C_2$–$C_{20}$ perfluoroalkyl radical, or a $C_5$–$C_{38}$ perfluoroalkyl radical having at least one ether oxygen atom; n is 1 to 3; m is 0 or 1; A is O, S, $CO_2$, $N(R_1)R_2$, $CON(R_1)R_2$, $SO_2N(R_1R_2$ or $(OCH_2CHR_3)_aO$; wherein a is 3 to about 15; $R_1$ is H or alkyl radical of 1 to about 4 carbon atoms; $R_2$ is $C_1$–$C_{12}$ alkylene; and $R_3$ is H or $CH_2Cl$; said process comprising reacting a fluorinated iodide of Formula I $$R_f-A_m-(CH_2)_n-I \qquad \text{I}$$

wherein $R_f$, A, m and n are as defined above, with a thiocyanate salt $M^+(SCN)^-$ wherein M is sodium or potassium, in the presence of a catalyst comprising a quaternary ammonium salt of formula $(R_4)_3(R_5)N^+Y^-$ wherein $R_4$ is butyl; $R_5$ is methyl or butyl; and Y is Cl, Br, I, or $HSO_4$; to yield the fluorinated thiocyanate of Formula II as defined above is disclosed.

9 Claims, No Drawings

FLUORINATED ALKYLTHIOCYANATE PROCESS

FIELD OF THE INVENTION

This invention relates to a novel phase transfer catalyzed conversion of fluorinated alkyliodides to the corresponding fluorinated alkyl thiocyanates.

BACKGROUND OF THE INVENTION

Perfluoroalkyl thiocyanates are useful intermediates for the preparation of perfluoroalkyl sulfonic acids by oxidation of the corresponding thiocyanate. The perfluoroalkyl sulfonic acids and their salts have uses as specialty surfactants and as sources of the corresponding sulfonyl derivatives. Reduction of perfluoroalkyl thiocyanates yields the corresponding perfluoroalkyl thiols. The perfluoroalkyl thiols are intermediates for the preparation of oil- and water-repellent compositions for textiles and paper products and for the preparation of fire extinguishing agents. Since the perfluoroalkyl thiocyanates are used in the preparation of multiple other compounds, an efficient means of making the thiocyanates is desirable.

UK patent 1,218,760 describes a process for the preparation of perfluoroalkylethyl thiocyanates from the corresponding perfluoroalkylethyl iodides using, inter alia, alcoholic solutions of potassium thiocyanate. The product is separated from inorganic potassium iodide and thiocyanate by filtration, and ethanol removed by distillation. The reaction is slow, requiring 15 to 30 hours at reflux and 12 hours of distillation to maximize product yield and quality. The yield of perfluoroalkylethyl thiocyanate is typically no better than 85%, fluorinated alkanes are formed which can complicate distillation, and free iodine is formed requiring special washing steps. Thorough removal of inorganic thiocyanate and iodide salts requires lengthy washing procedures.

Szonyi and Cambon (J. Fluorine Chemistry, 42, 59–68, 1989) applied phase transfer catalysis to prepare perfluoroalkylethyl thiocyanates from perfluoroalkylethyl iodides in the presence of an aqueous solution of potassium thiocyanate using trioctylmethylammonium chloride as the catalyst. The reactions, conducted in the absence of an organic solvent, were completed in 3–10 hours with yields as high as 96%. Although the distillation step is thus avoided, thorough removal of the quaternary ammonium catalyst by washing is extremely difficult.

In phase transfer catalysis, the catalyst, a quaternary ammonium or phosphonium salt, catalyzes the replacement of iodide with thiocyanate by the transfer of ion pairs between the aqueous and nonaqueous phases. Quaternary thiocyanate ion pairs are transferred from the aqueous phase and quaternary iodide pairs are transferred to the aqueous phase as the reaction proceeds. In the absence of the catalyst or solvent, anion transfer is negligible and the reaction does not proceed.

It is desirable m have a process to produce fluorinated alkyl thiocyanates by a fast phase transfer catalyzed process that provides high yields of a thiocyanate product without the need for flammable solvents and the concomitant final distillation step. It is also desirable to have such a phase transfer catalyzed process which provides for easy removal of the catalyst. The present invention provides such a process.

SUMMARY OF THE INVENTION

The present invention comprises a process for the preparation of a thiocyanate of Formula II $$R_f\text{—}A_m\text{—}(CH_2)_n\text{—}SCN \quad \text{II}$$

wherein $R_f$ is a $C_2$–$C_{20}$ perfluoroalkyl radical or a $C_5$–$C_{38}$ perfluoroalkyl radical having at least one ether oxygen atom, n is 1 to 3, m is 0 or 1, A is O, S, $CO_2$, $N(R_1)R_2$, $CON(R_1)R_2$, $SO_2N(R_1)R_2$ or $(OCH_2CHR_3)_aO$, wherein a is 3 to about 15, $R_1$ is H or alkyl radical of 1 to about 4 carbon atoms, $R_2$ is $C_1$–$C_{12}$ alkylene, and $R_3$ is H or $CH_2Cl$, said process comprising reacting a fluorinated iodide of Formula I $$R_f\text{—}A_m\text{—}(CH_2)_n\text{—}I \quad \text{I}$$

wherein $R_f$, A, m and n are as defined above, with a thiocyanate salt $M^+(SCN)^-$ wherein M is sodium or potassium, in the presence of a catalyst comprising a quaternary ammonium salt of formula $$(R_4)_3(R_5)N^+Y^-$$

wherein $R_4$ is butyl, $R_5$ is methyl or butyl, and Y is Cl, Br, I, or $HSO_4$, to yield the fluorinated thiocyanate of Formula II as defined above.

DETAILED DESCRIPTION OF THE INVENTION

The present invention comprises a process for the rapid preparation of fluorinated alkyl thiocyanates in high yield without the use of flammable solvents, without need for subsequent distillation, and in sufficiently high purity to allow ready hydrogenolysis to the corresponding fluorinated alkyl thiols.

The process of this invention converts fluorinated iodides of Formula I to thiocyanates of Formula II $$R_f\text{—}A_m\text{—}(CH_2)_n\text{—}I \quad \text{Formula I}$$
$$R_f\text{—}A_m\text{—}(CH_2)_n\text{—}SCN \quad \text{Formula II}$$

wherein $R_f$ is a $C_2$–$C_{20}$ perfluoroalkyl radical, or a $C_5$–$C_{38}$ perfluoroalkyl radical having at least one ether oxygen atom, n is 1 to 3, m is 0 or 1, A is O, S, $CO_2$, $N(R_1)R_2$, $CON(R_1)R_2$, $SO_2N(R_1)R_2$ or $(OCH_2CHR_3)_aO$, wherein a is 3 to about 15, $R_1$ is H or alkyl radical of 1 to about 4 carbon atoms, $R_2$ is $C_1$–$C_{12}$ alkylene, and $R_3$ is H or $CH_2Cl$.

The process of this invention uses as a catalyst at least one specifically chosen quaternary ammonium salt of the formula $(R_4)_3(R_5)N^+Y^-$ wherein $R_4$ is butyl, $R_5$ is methyl or butyl, and Y is Cl, Br, I, or $HSO_4$. The reaction catalyzed is a phase transfer reaction of thiocyanate ions from a concentrated aqueous phase containing an inorganic thiocyanate salt of the formula $M^+(SCN)^-$ to a water immiscible phase of a fluorinated alkyliodide of Formula I, or a mixture of said iodides. In the formula $M^+(SCN)^-$, M is an alkali metal of Group IA, preferably NaSCN or KSCN, and most preferably NaSCN. The reaction is carried out in the absence of a solvent to yield the corresponding fluorinated alkyl thiocyanate of Formula II. The reaction proceeds as shown in the reaction sequence below, which shows the specific case using sodium thiocyanate and a tetrabutylammonium bromide ($Bu_4N^+Br^-$) phase transfer catalyst.

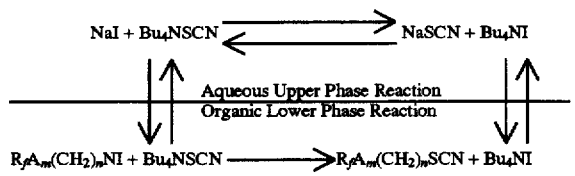

Preferred fluorinated alkyl iodides of Formula I comprise the perfluoroalkylethyl iodides of the formula $F(CF_2)_{2n}(CH_2)_2I$ wherein n is 1 to about 10, or mixtures of homologous series of such perfluoroalkylethyl iodides. The perfluoroalkylethyl iodide mixtures are commercially available, for instance as ZONYL TELB, TELB-L, and TELB-N Fluorochemical Intermediates from E. I. du Pont de Nemours and Company, Wilmington, Del. The compositions of these products are shown in Table 1.

TABLE 1

Homologue Composition for ZONYL TELB, TELB-L, and TELB-N Fluorochemical Intermediates

| | Approximate Weight % | | |
|---|---|---|---|
| | TELB | TELB-L | TELB-N |
| $F(CF_2)_{2n}(CH_2)_2I$ (Total) Value of n | 98.8 | >95 | 98 |
| 1 and 2 | 0.8 | <6 | — |
| 3 | 36 | 52–59 | 2 |
| 4 | 31 | >12 | 50 |
| =/>4 | — | <17 | — |
| 5 | 17.5 | — | 29 |
| =/>6 | 13.5 | — | 9.5 |
| $F(CF_2)_{2n}I$ (Total) | 0.4 | — | 0.3 |
| perfluorocarbon inerts | 0.7 | <5 | <0.8 |

< is less than, > is greater than, =/> is equal to or greater than

Tetraalkylphosphonium salts employed as phase transfer catalysts are typically more thermally stable than the corresponding tetraalkylammonium salts and allow reaction at higher temperatures. For the fluorinated alkylthiocyanate process of this invention, however, reaction temperatures are such that tetraalkylammonium salts are both adequate and much preferred due to lower cost. Similarly, although the aqueous solubility of potassium thiocyanate in water is higher than is the case for the sodium salt, sodium thiocyanate has adequate solubility and is thus preferred on the basis of cost.

The fluorinated alkyl thiocyanates prepared by the process of the present invention are used to produce the corresponding perfluoroalkyl thiols. A preferred method of hydrogenolysis for preparation of the thiols comprises reacting a perfluoroalkyl thiocyanate with hydrogen in the presence of a catalyst comprising a Group VIII metal or mixture thereof, or said metal in the presence of a modifier metal selected from the group consisting of a Group IB, Group IIB, Group IIIA, Group IVA, Group VA and Group VIA metal, or mixture thereof, said catalyst being on a porous insoluble support. The preferred catalyst is palladium, and useful supports include activated carbon, alumina, silica, aluminosilicates, zirconia, titania, calcium carbonate, zeolites and magnesia. When a modifier metal is present, the catalyst comprises 1% to 20% by weight of Group VIII metal and 0.2% to 5% by weight of modifier metal, the balance being the support component. When a modifier metal is not present the catalyst comprises 1% to 20% by weight of Group VIII metal, the remainder being the support component. Suitable solvents for the hydrogenolysis are polar and have a dielectric constant greater than 2. The reaction is conducted in a pressure vessel with heater, stirrer, pressure and temperature measuring devices, and inlet/outlet connections to metered gas supply lines. The thiocyanate is typically 30% to 60% by weight of the total charge to the reactor, the catalyst is 0.1% to 5%, and the balance is solvent optionally containing water. The molar ratio of substrate to catalyst is 25:1 to 2000:1 based on the Group VIII metal content of the catalyst. The reaction is conducted in a non-oxidizing atmosphere with hydrogen gas added as consumed. After reaction the product thiol is isolated by conventional means. This hydrogenolysis reaction is described in more detail in a copending application Ser. No. 08/629,824 filed Apr. 11, 1996.

Certain impurities are known to poison the Group VIII metal catalyst used in preparation of the thiols, and specifically to poison the preferred catalyst, palladium. It has been found that small amounts of residual phase transfer tetraalkylammonium catalyst remaining from the preparation of the thiocyanate by the process of the present invention will also poison Group VIII metal catalysts, either directly or by reason of the formation of tetraalkylammonium degradation products. It was found that greater than about 0.01 to 0.1 mole methyltricaprylammonium bromide, or of the preferred tetrabutylammonium bromide, per mole of palladium caused a decrease in activity. The preferred amount of residual phase transfer catalyst in the process of the present invention is 0.05 moles or less phase transfer catalyst/mole palladium. In the case of mixed perfluoroalkylethyl thiocyanate (for instance from ZONYL TELB Fluorochemical Intermediate, described in Table 1 above), for use in the hydrogenolysis procedure, a residual of catalyst in the fluorinated alkylthiocyanate in the process of the present invention of from about 1 to about 100 ppm, and preferably less than about 50 ppm after washing and drying, is preferred.

In the process of the present invention, the methyltributyl- or tetrabutylammonium salts are removable by water washing. Thus, the catalyst concentration is reduced in the washing step to provide a thiocyanate product effectively free of contaminants that would poison the Group VIII metal catalyst in the subsequent hydrogenolysis. By way of comparison, methyltrioctylammonium bromide and tetrapentylammonium bromide are sufficiently difficult to wash from the product that catalyst poisoning occurs. Certain other tetralkylammonium salts, for instance tetrahexylammonium and tetraoctylammonium tend to cause a stable emulsion to form during the agitation necessary in the phase transfer catalyzed reaction. Tetramethylammonium bromide, tetraethylammonium bromide, and tetrapropylammonium bromide are ineffective phase transfer catalysts for the process of the present invention. Methyltributylammonium bromide is effective for fluorinated alkyl iodide homologues of 6 carbon atoms or less, but tends to be slow for higher homologues of 8 carbon atoms or more. The preferred catalyst, in the process of the present invention, tetrabutylammonium bromide, is more effective with mixtures of higher homologues.

The process of the present invention provides the desired product sufficiently free of catalyst impurities that, otherwise, poison the preferred Group VIII metal catalyst, palladium, used in subsequent hydrogenolysis to prepare the corresponding fluorinated alkyl thiols. Additionally, the process of this invention provides very high yield and conversion of the fluorinated alkyl iodides to the corresponding fluorinated alkyl thiocyanates.

The preferred process of this invention comprises a two stage reaction sequence wherein a first stage comprises 1) reacting a fluorinated iodide of Formula I as defined above with a thiocyanate salt $M^+(SCN)^-$ as defined above in the presence of a catalyst $(R_4)_3R_5N^+Y^-$ as defined above to generate a fluorinated alkyl thiocyanate of Formula II as defined above in a yield of from about 80% to about 95% and 2) isolating the thiocyanate and residual catalyst, and a second stage comprising repeating steps 1) and 2) of stage one to generate the fluorinated thiocyanate of Formula II in an overall yield of from about 98% to about 99.9%. Multiple washes of the reaction mix with water are conducted with the water temperature maintained at from about 85° C. to about 120° C., and preferably from about 85° C. to about 95° C., during both reaction stages. A temperature of at least about 80° C. ensures all the fluorinated alkyl iodide is melted and the fluorinated alkyl phase is homogeneous. Temperatures less than about 80° C. can result in impaired phase separation, making the subsequent removal of the aqueous phase more difficult. Reactions and washing steps conducted at temperatures above 100° C. are conducted under pressure to prevent water from boiling off during the reaction and washing stages and to prevent components of the reaction mass steam distilling or subliming onto cooler parts of the equipment. The ingredients are mixed and reacted in the first stage, analyzed by gas chromatography (GC), washed repeatedly with water, and reacted again in the second stage with additional aqueous alkali metal thiocyanate and phase transfer catalyst. The product is again analyzed by GC, thoroughly washed, and dried by purging while hot with nitrogen.

The reactants are mixed by charging a suitable reactor equipped with an agitator and heated to the temperature range of from about 85° C. to about 120° C., with a solution of water and the alkali metal thiocyanate salt. The fluorinated alkyl iodide is melted and added while maintaining the temperature range specified above. The ratio of water to thiocyanate salt is between about 1:3 and about 3:1, preferably about 1:1, by weight. Lower alkali thiocyanate concentrations slow the reaction and increase the reactant volume, higher concentrations reduce the difference in phase densities and can make subsequent phase separation more difficult. The amount of thiocyanate salt added at the first stage is based on the molar amount of fluorinated alkyl iodide used.

The molar ratio of thiocyanate salt to fluorinated iodide for the first reaction stage is between about 2:1 and about 1:1 and preferably about 1:1. Higher ratios have little effect and waste the thiocyanate salt. Lower ratios cause less complete reaction in the first stage reducing the first stage conversion. A reduced first stage conversion can reduce the overall conversion. The amount of tetraalkylammonium salt added is also in molar proportion to the amount of fluorinated alkyl iodide, and the molar ratio of the catalyst to iodide is between about 1:100 and about 1:10, preferably about 1:40. Higher ratios waste the catalyst, lower concentrations slow the reaction.

Adequate agitation is necessary during the reaction. Typically, a power input of about 1.0–5.0 HP/1000 gal. (200–1000 kW/m$^3$), and preferably about 3 HP/1000 gal (600 kW/m$^3$) is sufficient, but the optimum agitation may be dependent on the reactor and agitator design. Insufficient agitation causes the reaction to proceed too slowly, excessive agitation wastes power. Methods for establishing the optimum agitation for a specific equipment set are well known in the art, and are described in the literature, for instance Starks and Owens in J. Am. Chem. Soc., 95, 3613–3617, 1973, and Solaro, et al., in J. Org. Chem., 45, 4179–4183, 1980.

The order of addition of the components is not critical, although it is typically more convenient to premix and heat the water and the alkali metal thiocyanate. The ingredient mixture is agitated as described above and the temperature maintained in the range described above for 3 to 10 hours. The longer times are necessary to complete conversion of the higher molecular weight components of the homologous series of fluorinated alkyl iodides. The reaction mixture is monitored by GC analysis, allowing both the formation of the fluorinated alkyl thiocyanate product and the disappearance of the fluorinated alkyl iodide to be measured. Typically, the reaction is 85% to 95% complete at the end of the first stage. Any residual catalyst present in the reaction mixture containing the fluorinated alkylthiocyanate after completion of the reaction is removed by phase separation and washing with water.

The reaction mass separates into two phases when agitation is stopped. Normally the aqueous phase is the less dense supernatant, and this is readily confirmed by diluting a small sample of the supernatant with a larger volume, for instance 10–20 volumes, of water. The aqueous phase shows no denser oil phase when thus diluted. Throughout all the washing and separation steps, temperatures are maintained in the reaction temperature range described above. Lower temperatures can cause selective precipitation of reactants resulting in selective conversion, and, during the washing steps, may impair the phase separation. Should a low temperature excursion occur, temperatures are returned to the correct range to reverse these effects before proceeding. Optionally, up to one volume of hot water (at the reaction temperature) is added to facilitate phase separation at the end of the first stage, but this is not normally necessary. The product fluorinated alkyl thiocyanate phase is washed with an equal volume of preheated water, the wash is removed by a suitable method, for instance by suction or by a siphon. The retained lower phase is then washed twice more with the same amount of preheated water.

To the retained and thrice-washed reaction mass, maintained in the reaction temperature range, is added additional preheated aqueous alkali metal thiocyanate and phase transfer catalyst. The ratio of water to alkali metal thiocyanate is as for stage 1. For the second stage, the molar ratio of thiocyanate salt to original fluorinated iodide (amount used in the first stage) is between about 0.5:1 and about 0.2:1 and preferably about 0.3:1. The higher ratios are desired if first stage conversion is 93% or less. The molar ratio of phase transfer catalyst added for the second stage is between about 1:300 and about 1:30, preferably about 1:120. As for the first stage, the order of addition is not critical, although it is typically more convenient to premix and heat the water and the alkali metal thiocyanate.

The reaction temperature and agitation rate are maintained for 2–3 hours, until GC analysis shows conversion is at least about 98% and preferably about 99.9% complete.

The supernatant aqueous layer is removed as after the first stage. The retained hot product from the second stage is washed repeatedly with preheated water as in the washings following the first stage. Typically 4 to 8 washes are performed at this stage, and preferably six. The washing steps are varied by those skilled in the art to achieve any specifications for residual catalyst or other impurities. The above procedure typically generates a thiocyanate product in which residual catalyst cannot be detected by proton nuclear magnetic resonance (proton NMR) spectroscopy.

The test for adequate washing is the production of thiocyanate product that can be converted by hydrogenolysis (via the procedure of U.S. Ser. No. 08/629,824 as previously described) to at least 98% and preferably at least 99.5% yield of thiol using the preferred 1:900 ratio of Group VIII metal catalyst to thiocyanate. Inadequately washed thiocyanate product containing excessive amounts of residual phase transfer catalyst, causes poorer hydrogenolysis conversion to the thiol or requires higher and uneconomic ratios of group VIII metal catalyst.

The solubility of water in the hot washed fluorinated alkyl thiocyanate is very low, and the product is readily dried by purging with a nitrogen stream while the molten thiocyanate product is held at about 95° C. The purge stream is passed down an ambient temperature condenser, and the purged water removed. The purging is continued until water stops condensing. The molten thiocyanate product is discharged into suitable containers and freezes on cooling.

The process of the present invention is useful to prepare perfluoroalkyl thiocyanates in high yield without the need for use of flammable solvents and their subsequent removal via distillation. The product perfluoroalkyl thiocyanates are useful in the production of perfluoroalkyl sulfonic acids used as surfactants, and in the production of perfluoroalkyl thiols used in making oil- and water-repellant compositions for textiles and paper.

Examples 1–3 below demonstrate the practice of this invention and the advantage of the preferred catalysts of this invention versus other tetraalkyl ammonium salts used in Comparative Examples A–H. In the examples, the following approximate relationship exists between stirring rate and power for a 1-liter resin flask with 2⅛" (5.4 cm) impeller.

Stirrer speed: 200 rpm=~0.5 HP/1000 gal (~100k W/m$^3$) (inadequate)
400 rpm=~3 HP/1000 gal (~600 kW/m$^3$) (adequate)
600 rpm=>5 HP/1000 gal (>1000 kW/m$^3$) (more than adequate)

EXAMPLES

Example 1

Preparation of Mixed Perfluoroalkylethyl Thiocyanates with Tetrabutylammonium Bromide Catalyst A 1000-ml resin flask equipped with overhead stirrer, heating mantle, and warm (60° C.) temperature water condenser was charged with ZONYL TELB Fluorochemical Intermediate (see Table 1 above, 303 g, 0.6 mole) available from E. I. du Pont de Nemours and Company, Wilmington, Del., sodium thiocyanate (48.6 g, 0.60 mole, 'Baker-analyzed' A.C.S. reagent, 98.6% from J. T. Baker, Inc. Phillipsburg, N.J.) dissolved in water (48 g), and tetrabutylammonium bromide (4.8 g, 0.015 mole, Aldrich Chemical Co., Milwaukee, Wis., 99%). The solution was then heated to 95° C. with stirring at 600 rpm. The reaction rate was monitored by GC analysis and at the end of four hours, the reaction was 94% complete. Water (300 g) was then added to the mixture to break the emulsion, the whole heated to 95° C. at 600 rpm for 15 minutes, and then the aqueous phase removed via suction.

The reaction product was washed with two additional water washes (300 g) as above at 95° C. and the supernatant aqueous wash removed via suction after each wash. Sodium thiocyanate (15 g, 0.19 mole) in water (15 g) was then added together with tetrabutylammonium bromide (1.4 g, 0.0044 mole). The reaction mixture was then stirred at 95° C. and 600 rpm for two more hours. At this point a gas chromatographic analysis showed the reaction was 99.9% complete. Water (300 g) was then added and the whole stirred at 95° C. for 15 minutes and the aqueous phase removed. Five additional water washes (300 g) were each carried out for 15 minutes. After water removal by suction, the solutions were purged with nitrogen at 95° C. to remove traces of water. No phase transfer catalyst or its decomposition products were detected by proton NMR in the final product.

A palladium catalyzed hydrogenolysis of the final product, as described above, showed a 99.5% yield of thiol product.

Example 2

Preparation of Mixed Perfluoroalkylethyl Thiocyanates with Tetrabutylammonium Bromide Catalyst The same reactor as in Example 1 was charged with ZONYL TELB-N Fluorochemical Intermediate (see Table 1 above, 473.2 g, 0.78 mole), sodium thiocyanate (63.2 g, 0.78 mole) in water (63 g), and tetrabutylammonium bromide (6.24 g, 0.02 mole) and reacted at 95° C. with 600 rpm stirring speed for 6 hours with temperature maintained at 95° C. until 97% conversion was obtained. The reaction product was washed with three water washes, each 390 g with removal of the water via suction after each wash. Sodium thiocyanate (19.5 g, 0.24 mole) in 19.2 g water and tetrabutylammonium bromide (1.8 g, 0.0056 mole) were added and the solution stirred an additional two hours at 95° C. to give a 99.9% yield of perfluoroalkyl thiocyanate. The water was removed as in Example 1 and hydrogenolysis as in Example 1 showed greater than 99.5% yield of thiol.

Example 3

Preparation of Mixed Perfluoroalkylethyl Thiocyanates with Tetrabutylammonium Bromide Catalyst Example 2 was repeated except that the two phases were stirred at 400 rpm instead of 600 rpm. Stirring was continued for 8 hours until 92% conversion was obtained. The reaction product was washed, treated with additional sodium thiocyanate and tetrabutylammonium bromide as in Example 2 and the solution was stirred an additional two hours at 400 rpm to give a 99.9% conversion to perfluoroalkyl thiocyanate. The product was washed and subjected to hydrogenolysis as in Example 2 to give a 99.5% yield of thiol.

Comparative Example A

Preparation of a Sample of Mixed Perfluoroalkylethyl Thiocyanates with Tricaprylmethylammonium Bromide The process of Example 2 was repeated substituting Aliquat 336 (tricaprylmethylammonium chloride, 8.1 g, 0.02 mole, from Aldrich Chemical Co., Milwaukee, Wis.) for tetrabutylammonium bromide. The conversion measured by GC analysis was 99.9% in 11 hr. and the washing and drying were carried out in the same way as Example 2. However, the proton NMR of the final product showed 0.02 mole of the Aliquat 336 per mole of product remaining (about 80% of the amount of catalyst used), corresponding to about 1.5% residual catalyst by weight in the product. The metal catalyzed hydrogenolysis reaction showed no conversion.

This example demonstrated tricaprylmethylammonium bromide was difficult to remove from the product and subsequently poisoned the hydrogenation catalyst used to prepare the corresponding thiol.

Comparative Example B

Attempted Preparation of a Sample of Mixed Perfluoroalkylethyl Thiocyanates with Tetrapropylammonium Bromide The process of Example 2 was repeated substituting tetrapropylammonium bromide (5.3 g, 0.02 mole from Aldrich Chemical Co., Milwaukee, Wis, 98% purity). No reaction was observed in 5 hours, indicating the catalyst was ineffective for this reaction.

Comparative Example C

Preparation of a Sample of Mixed Perfluoroalkylethyl Thiocyanates With Tetrahexylammonium Bromide The process of Example 2 was repeated substituting tetrahexylammonium bromide (8.7 g, 0.02 mole from Aldrich Chemical Co., Milwaukee, Wis., 99% purity). The reaction was observed for 8 hours until 99.8% conversion to perfluoroalkyl thiocyanate was obtained. On attempted water wash an emulsion formed which was still present after one hour, indicating isolation of a catalyst-free product suitable for subsequent hydrogenolysis by water washing was not practical. No further purification was done.

Comparative Example D

Preparation of a Sample of Mixed Perfluoroalkylethyl Thiocyanates with Tetrapentylammonium Bromide Example 2 was repeated substituting tetrapentylammonium bromide (7.6 g, 0.02 mole from Sigma-Aldrich, Milwaukee, Wis. The reaction to yield perfluoroalkyl thiocyanate was complete in 7 hours. After purification, no phase transfer catalyst was observed by proton NMR. On attempted hydrogenolysis no conversion to thiol was observed, indicating that, although the amount of phase transfer catalyst was below the detection limit of the NMR, the product was not suitable for subsequent hydrogenolysis.

Comparative Example E

Attempted Preparation of a Sample of Mixed Perfluoroalkylethyl Thiocyanates with Methyltributylammonium Chloride Example 1 was repeated but methyltributylammonium chloride was substituted for tetrabutylammonium bromide. Only a 21% conversion to perfluoroalkyl thiocyanate was observed after 21 hours, indicating the catalyst was inferior to the that in the process of Example 1, and the reaction was stopped.

Comparative Example F

Attempted Preparation of a Sample of Mixed Perfluoroalkylethyl Thiocyanates with Methyltributylammonium Chloride Example 2 was repeated substituting methyltributylammonium chloride for tetrabutylammonium bromide. No product was observed in five hours, indicating the catalyst was inferior to that in the process of Example 2.

Comparative Example G

Preparation of a Sample of 2-Perfluorohexylethyl Thiocyanate with Methyltributylammonium Chloride Comparative Example D was repeated substituting 2-perfluorohexylethyl iodide for Zonyl TELB Fluorochemical Intermediate. A 74% conversion to perfluoroalkyl thiocyanate was obtained in 6 hours, indicating the catalyst, although more effective on 2-perfluorohexylethyl iodide than on the higher homologues present in ZONYL TELB Fluorochemical Intermediate, was inferior to that in the process of Example 1.

Comparative Example H

Attempted Preparation of Mixed Perfluoroalkylethyl Thiocyanates with Tetrabutylammonium Bromide Catalyst with Slower Stirring Example 2 was repeated except that the two phases were stirred at 200 rpm instead of 600 rpm. The reaction was only 28% complete after 12 hours and was stopped.

What is claimed is:

1. A process for the preparation of a thiocyanate of Formula II $$R_f\text{—}A_m\text{—}(CH_2)_n\text{—}SCN \qquad II$$

wherein $R_f$ is a $C_2$–$C_{20}$ perfluoroalkyl radical, or a $C_5$–$C_{38}$ perfluoroalkyl radical having at least one ether oxygen atom, n is 1 to 3, m is 0 or 1, A is O, S, $CO_2$, $N(R_1)R_2$, $CON(R_1)R_2$, $SO_2N(R_1)R_2$ or $(OCH_2CHR_3)_aO$, wherein a is 3 to about 15, $R_1$ is H or alkyl radical of 1 to about 4 carbon atoms, $R_2$ is $C_1$–$C_{12}$ alkylene, and $R_3$ is H or $CH_2Cl$, said process comprising reacting a fluorinated iodide of Formula I $$R_f\text{—}A_m\text{—}(CH_2)_n\text{—}I \qquad I$$

wherein $R_f$, A, m and n are as defined above, with a thiocyanate salt $M^+(SCN)^-$ wherein M is sodium or potassium, in the presence of a catalyst comprising a quaternary ammonium salt of formula $$(R_4)_3(R_5)N^+Y^-$$

wherein $R_4$ is butyl, $R_5$ is methyl or butyl, and Y is Cl, Br, I, or $HSO_4$, to yield the fluorinated thiocyanate of Formula II as defined above, and removing residual catalyst from a reaction mixture containing the fluorinated thiocyanate after completion of the reaction by phase separation and washing with water.

2. The process of claim 1 wherein the catalyst is tetrabutylammonium chloride, tetrabutylammonium bromide, or methyltributylammonium chloride.

3. The process of claim 1 conducted at a temperature from about 85° C. to about 120° C.

4. The process of claim 1 wherein the wash water is maintained at a temperature of from about 85° C. to about 95° C.

5. The process of claim 1 wherein the amount of residual catalyst is a maximum of about 100 ppm by weight in the fluorinated alkyl thiocyanate.

6. The process of claim 1 wherein the molar ratio of thiocyanate salt to fluorinated iodide is from about 2:1 to about 1:1.

7. A process for the preparation of a thiocyanate of Formula II $$R_f\text{—}A_m\text{—}(CH_2)_n\text{—}SCN \qquad II$$

wherein $R_f$ is a $C_2$–$C_{20}$ perfluoroalkyl radical, or a $C_5$–$C_{38}$ perfluoroalkyl radical having at least one ether oxygen atom, n is 1 to 3, m is 0 or 1, A is O, S, $CO_2$, $N(R_1)R_2$, $CON(R_1)R_2$, $SO_2N(R_1)R_2$ or $(OCH_2CHR_3)_aO$, wherein a is 3 to about 15, $R_1$ is H or alkyl radical of 1 to about 4 carbon atoms, $R_2$ is $C_1$–$C_{12}$ alkylene, and $R_3$ is H or $CH_2Cl$, said process conducted in two phases wherein a first stage comprises 1) reacting a fluorinated iodide of Formula I $$R_f\text{—}A_m\text{—}(CH_2)_n\text{—}I \qquad I$$

wherein $R_f$, A, m and n are as defined above, with a thiocyanate salt $M^+(SCN)^-$ wherein M is sodium or potassium, in the presence of a catalyst comprising a quaternary ammonium salt of Formula $$(R_4)_3(R_5)N^+Y^-$$

wherein $R_4$ is butyl, $R_5$ is methyl or butyl, and Y is Cl, Br, I, or $HSO_4$, to yield the fluorinated thiocyanate of Formula II as defined above in yield of from about 80% to about 95%, and 2) isolating said thiocyanate and residual catalyst, and a second stage comprises repeating steps 1) and 2) of stage one to generate said fluorinated alkyl thiocyanate in an overall yield of from about 98% to about 99.9%.

8. The process of claim 7 wherein the molar ratio of the thiocyanate salt to fluorinated iodide is about 1:1 in the first stage, and in the second stage is about 0.3:1 based on the amount of fluorinated iodide used in the first stage.

9. The process of claim 1 wherein the thiocyanate product is a perfluoroalkylethyl thiocyanate mixture.

* * * * *

UNITED STATES PATENT AND TRADEMARK OFFICE
CERTIFICATE OF CORRECTION

PATENT NO : 5,726,337
DATED : March 10, 1998
INVENTOR(S) : Jacobson

It is certified that error appears in the above-identified patent and that said Letters Patent is hereby corrected as shown below:

Column 8, line 51, replace "Bromide" with –Chloride–
Column 8, line 65, replace "bromide" with –chloride–
Column 11, line 6, replace "$R_2$" with –$R_3$–

Signed and Sealed this

Fifteenth Day of February, 2000

Q. TODD DICKINSON

*Attest:*

*Attesting Officer*     *Commissioner of Patents and Trademarks*